(12) United States Patent
Weiler

(10) Patent No.: US 6,264,694 B1
(45) Date of Patent: Jul. 24, 2001

(54) SOFT TISSUE GRAFT FIXATION DEVICE AND METHOD

(75) Inventor: Andreas Weiler, Berlin (DE)

(73) Assignee: Linvatec Corporation, Largo, FL (US)

( * ) Notice: Subject to any disclaimer, the term of this patent is extended or adjusted under 35 U.S.C. 154(b) by 0 days.

(21) Appl. No.: 09/248,812

(22) Filed: Feb. 11, 1999

(51) Int. Cl.[7] ........................................... A61F 2/08
(52) U.S. Cl. ......................................... 623/13.14
(58) Field of Search .................... 623/23.11, 13.11, 623/13.12, 13.13, 13.14, 13.18, 23.12, 23.48, 23.13, 23.14, 23.23, 22.43, 22.44, 22.45, 22.46, 16.11, 17.11, 17.12, 17.16, 5.11

(56) References Cited

U.S. PATENT DOCUMENTS

| | | | |
|---|---|---|---|
| 2,765,787 | * 10/1956 | Pellet ........................... | 623/21 |
| 3,638,243 | * 2/1972 | Campbell ..................... | 623/21 |
| 4,198,711 | * 4/1980 | Zeibig .......................... | 623/21 |
| 4,634,445 | * 1/1987 | Helal ............................ | 623/21 |
| 4,744,793 | * 5/1988 | Parr .............................. | 623/13.14 |
| 4,753,657 | * 6/1988 | Lee ............................... | 623/16 |
| 4,828,562 | * 5/1989 | Kenna .......................... | 623/13.14 |
| 4,936,848 | * 6/1990 | Bagby ........................... | 623/17 |
| 5,356,435 | * 10/1994 | Thein ............................ | 623/15 |
| 5,425,767 | * 6/1995 | Steininger .................... | 623/13.14 |
| 5,702,474 | * 12/1997 | McCandliss .................. | 623/23 |
| 5,755,797 | * 5/1998 | Baumgartner ................ | 623/17 |
| 5,951,604 | * 9/1999 | Scheker ........................ | 623/21 |
| 5,984,966 | * 11/1999 | Kiema .......................... | 623/13.14 |
| 5,993,486 | * 11/1999 | Tomatsu ....................... | 623/13 |
| 6,099,530 | * 8/2000 | Simonian ..................... | 623/13.14 |

\* cited by examiner

*Primary Examiner*—Michael J. Milano
(74) *Attorney, Agent, or Firm*—Gene Warzecha

(57) ABSTRACT

An auxiliary graft fixation device for use with an interference screw to secure soft tissue ligament grafts within a bone tunnel. The device is in the form of a spherical member having a throughbore which enables it to be tied to the end of a soft tissue graft. The device enables it to be pulled into the bone tunnel with the soft tissue ligament graft while enabling the graft to be secured within the bone tunnel by an interference screw and preventing the graft from sliding past the interference screw and out of the tunnel.

11 Claims, 2 Drawing Sheets

SOFT TISSUE GRAFT FIXATION DEVICE AND METHOD

BACKGROUND OF THE INVENTION

1. Field of the Invention

The invention relates to surgical implant devices. More particularly, the invention relates to arthroscopically usable surgical implant devices suitable for fixation of ligament grafts within bone tunnels. Still more particularly, the invention relates to devices and methods for the arthroscopic reconstruction of ligaments using soft tissue ligament grafts.

2. Description of the Prior Art

The reconstruction of ligaments including anterior cruciate ligaments (ACL) and posterior cruciate ligaments (PCL) using autologous ligament grafts, allografts or artificial grafts is well known. The ACL and PCL procedures may be performed arthroscopically and generally involve preparing a bone tunnel through the tibia and adjacent femur, placing a ligament graft extending between the two bone tunnels and securing each end of the graft within its respective tunnel.

One common method of ACL reconstruction employs the use of bone-tendon-bone (BTB) ligament grafts (harvested from the patella and tibia) where the bone block at each end of the graft is fixed within its respective tunnel by an interference screw secured within each tunnel between the tunnel wall and the adjacent bone block. The interference screw is aligned parallel to the axis of the tunnel and holds the bone block in the tunnel by wedging it against the tunnel wall opposite the screw and by engaging the bone block and the adjacent tunnel wall with the screw threads. Another common method employs the use of soft tissue grafts (semitendinosus, hamstring, achilles, quadriceps, etc.) where the ends of the graft are secured by an interference screw similarly interposed between the wall of the bone tunnel and the adjacent soft tissue of the graft.

One difference between the BTB and soft tissue graft procedures is that in the latter the screw merely deforms the resilient soft tissue temporarily. Thus, while the use of interference screws for ACL fixation is widely preferred over other methods, recent clinical and laboratory experience has found that soft tissue grafts secured with only an interference screw may experience graft laxity over time. This may result in loss of the requisite tension in the graft and consequent re-operation. One possible reason for graft laxity may be the longitudinal movement of the graft within the tunnel and past the interference screw during cyclic fatigue before healing occurs. This type of graft slippage does not occur in BTB grafts because the bone block attached to the tendon is positively engaged by the screw threads and cannot move beyond the interference screw.

Despite the possibility of graft laxity, soft tissue grafts are still viewed as beneficial because they do not leave the patella in a weakened state like BTB grafts.

It is accordingly an object of this invention to produce a device and method for securing a soft tissue ligament graft within a bone tunnel so as to prevent graft slippage from the tunnel.

It is another object of this invention to produce a device and method for providing additional secondary fixation to a soft tissue ligament graft secured within a bone tunnel by a primary fixation device.

It is a further object of this invention to produce a device and method for assuring that a soft tissue ligament graft secured in a bone tunnel by an interference screw remains secured by preventing the soft tissue graft from moving past the interference screw.

SUMMARY OF THE INVENTION

These and other objects of this invention are achieved by the preferred embodiment of the device and method disclosed herein. The device comprises a member which is designed to be attached to the end of a ligament graft in a bone tunnel in order to act as a "brake" against movement of the graft out of the tunnel. In the preferred embodiment, the device has approximately the same diameter as the bone tunnel and is attached to the graft with suture and then pulled into the femoral tunnel. An interference screw is then inserted next to the graft in the tunnel until it contacts the device thus capturing the device in the tunnel. The device anchors the soft tissue graft into the femoral tunnel and does not allow it to move past the interference screw. Any attempted movement of the graft out of the tunnel is resisted by the contact between the device and the interference screw.

In a preferred embodiment the device is a spherical member having a diameter approximately equal to that of the tunnel and a throughbore to facilitate tying the device to the end of the ligament graft.

DESCRIPTION OF THE PREFERRED EMBODIMENT

Figure 1:
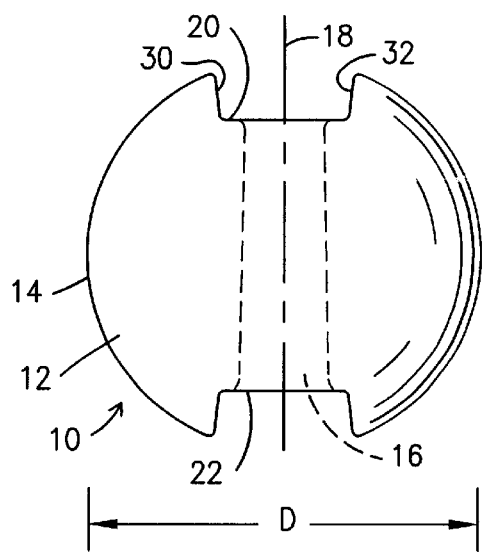
FIG. 1 is a front elevation view of a surgical implant constructed in accordance with the principles of this invention.
Figure 2:
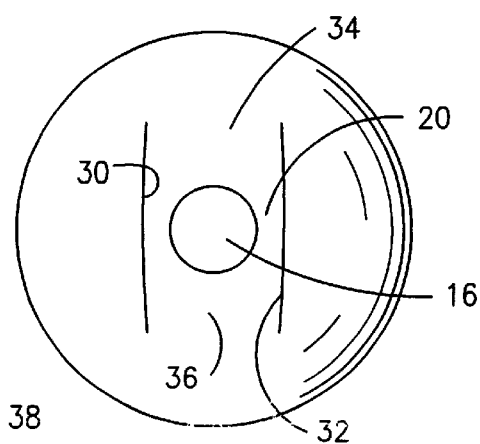
FIG. 2 is a top plan view of FIG. 1.
Figure 3:
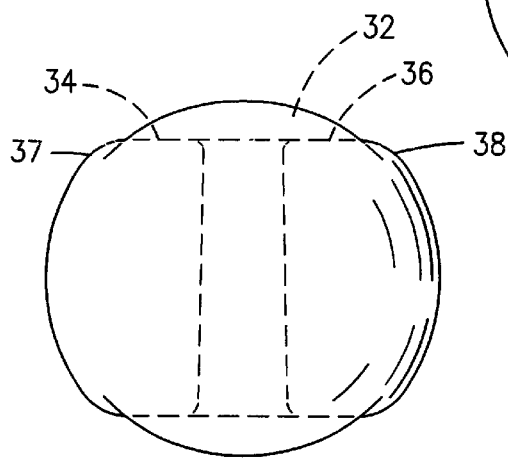
FIG. 3 is a side elevation view of FIG. 1.

Referring to FIGS. 1 through 3, surgical implant 10 comprises a body 12 having a spherical exterior surface 14, and a throughbore 16 aligned along the axis 18 of the body. Throughbore 16 intersects with a flat surface 20 adjacent one end thereof and a flat surface 22 adjacent the other end. While throughbore 16 may be a cylindrical bore, in the preferred embodiment it is tapered (to facilitate manufacture by molding) so that the diameter of throughbore 16 adjacent surface 20 is slightly smaller than the diameter adjacent surface 22. Each surface 20 and 22 is perpendicular to axis 18 and recessed a predetermined distance from the spherical surface 14. Consequently, surface 20 is bounded by parallel walls 30 and 32 and has ends 34 and 36 which are adjacent to and smoothly blend into spherical surface 14 at 37 and 38, respectively. Surface 22 is similarly structured. The recesses provide clearance for suture passing through the bore thus enabling the diameter D to equal the diameter of the bone tunnel with which the device is to be used causing suture to be squeezed between the implant and the tunnel wall.

Figure 4:
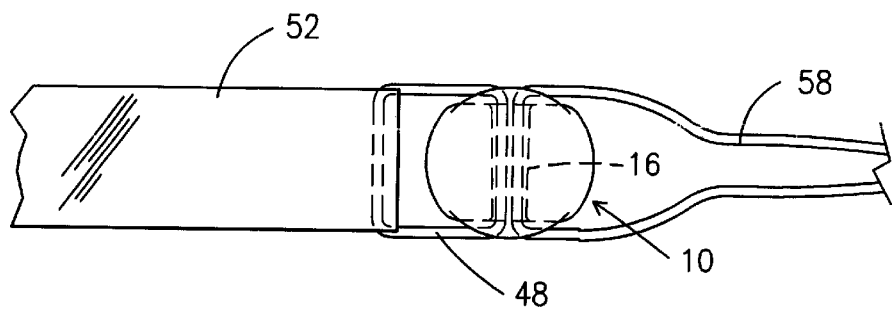
FIG. 4 is a side elevation view of the implant of FIG. 1 attached to a ligament graft.
Figure 5:
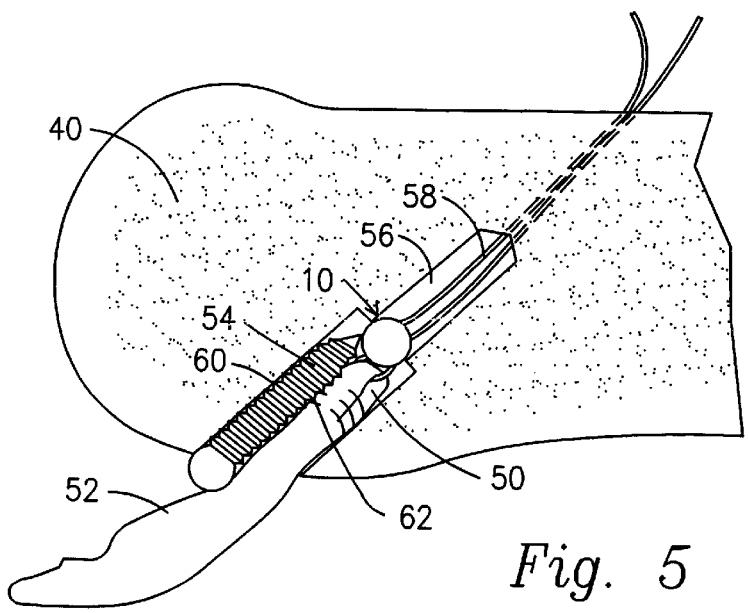
FIG. 5 is a diagram of a soft tissue ligament graft within a bone tunnel adjacent an interference screw and the surgical implant shown in FIG. 1.

The implant 10 may be used during conventional arthroscopic reconstruction of a ligament graft. This conventional procedure entails the preparation of a bone tunnel through the tibia and into the femur. The femoral end of the tunnel will generally have a small axially aligned hole drilled through the femur so that a pin could extend through both tunnels, between the outside lateral surface of the leg and the entrance to the tibial tunnel. The sutures attached to the ligament graft are attached to the tibial end of this pin and it is then used to pull the graft through the tibial tunnel and into place in both tunnels. When using the invention, however, some modification of the conventional procedure is helpful. First, the tunnel should be made deeper to accommodate the diameter of the implant 10. For example, if the surgeon's preference is to use a 25 mm interference screw in a 9 mm tunnel, a 9 mm implant would be used and the femoral tunnel length should be made at least equal to the length of the screw plus the diameter of the implant, or 34 mm. To accommodate clearance for suture extending between the implant and the graft, the tunnel length may be greater. An implant 10 having a diameter equal to that of the femoral tunnel is first secured by suture 48 to the femoral end of the ligament graft 52 before it is pulled into the tunnels. The assembled implant/graft, best seen in FIG. 4, is then pulled into place by the suture 58 extending from the lateral femur into the position shown in FIG. 4. As shown in FIG. 5, showing the invention within a femur 40 (not showing the tibial end), implant 10 is tied to the femoral end 50 of ligament graft 52 which is secured by interference screw 54. FIG. 5 shows the stage in the procedure after the implant/graft assembly has been pulled into femoral tunnel 56 by suture 58. It will be noted that the interference screw is partially embedded in the tunnel wall at 60 and partially embedded in the soft tissue graft at 62. The portion of the screw from its axis to area 62 extends transversely toward the opposing wall of the tunnel, thus squeezing the graft into a space smaller than the original tunnel size. Since the implant 10 is situated distally of the screw in an unrestricted area of the tunnel in contact with the tip of the interference screw, the implant will not move toward the tunnel entrance, thus acting with the screw to hold the graft firmly in place.

In the preferred embodiment, implant 10 is a cannulated, sterile, single-use fixation device made from a bioabsorbable polymer (e.g. Poly (L-lactic) acid) that will gradually be metabolized by the body. While it is intended to be used, in conjunction with a bioabsorbable interference screw, as a back-up to interference screw fixation of soft tissue grafts on the femoral side of a ligament reconstruction, other uses may arise. Indeed, one might even use the invention with a BTB graft.

Bone tunnels are usually formed by a drilling process and the spherical shape of implant 10 facilitates its passage through a cylindrical bone tunnel having a diameter equal to or slightly larger than that of the implant. It will be understood, however, that so long as the implant is large enough in a dimension transverse to the axis of the tunnel any shape could be utilized because, once the implant and interference screw are in place, the implant would then not be able to be pulled past the interference screw.

It will be understood by those skilled in the art that numerous improvements and modifications may be made to the preferred embodiment of the invention disclosed herein without departing from the spirit and scope thereof.

What is claimed is:

1. A surgical implant comprising:
   a bioabsorbable spherical member having an axial throughbore, said spherical member having an external spherical surface wherein said surface is, adjacent each end of said throughbore, recessed relative to the non-adjacent spherical surface, and wherein said recess comprises a rectangular surface symmetrically situated about said throughbore, said rectangular surface smoothly blending at two opposing ends into said spherical surface and at the other two opposing ends into a surface extending between said rectangular surface and said spherical surface.

2. A surgical implant according to claim 1 wherein said throughbore has a first predetermined diameter at one end thereof and a second predetermined diameter at the other end thereof, said first predetermined diameter being greater than said second predetermined diameter.

3. A surgical implant according to claim 1 wherein said recess comprises a flat surface the plane of which is perpendicular to the axis of said throughbore.

4. In combination, a secondary implant and a primary implant, said secondary surgical implant for use with said primary surgical implant in a bone tunnel having an axis, a first predetermined diameter along the length of said tunnel, a proximal end and a distal end, said primary surgical implant engaging a ligament graft within said bone tunnel, said ligament graft being in alignment with said axis and occupying a predetermined amount of space within said tunnel such that the transverse cross-sectional area of the graft-occupied portion of said tunnel comprises a first predetermined size at a first point adjacent said primary implant, said first predetermined size being less than that of the graft-unoccupied portion of said tunnel at a second point adjacent the distal end of the tunnel, said second point being distal of said primary surgical implant and longitudinally spaced distally from said first point, said secondary implant comprising:
   a body having a second predetermined size smaller than said first diameter to enable said body to fit within said bone tunnel distal end but greater than said first predetermined size whereby said body is too large to come out of said bone tunnel past said primary surgical implant; and
   means to enable said body to be secured to said ligament graft.

5. A secondary implant according to claim 4 wherein said means to enable said body to be secured to said ligament graft comprises a throughbore in said body.

6. In a method for securing a ligament graft in a bone tunnel, having a first predetermined transverse area, to prevent longitudinal motion of said graft in said tunnel by constricting at least a portion of said ligament graft with a first device into a second predetermined transverse area within said tunnel, said second predetermined transverse area being smaller than said first predetermined transverse area, the improvement comprising the steps of:
   securing to one end of said ligament graft a second device, having a size greater than said second predetermined transverse area, prior to placing said second device into said bone tunnel; and
   inserting said first device into said tunnel, in constricting opposition to said ligament graft, after said second device and ligament graft have been placed into said tunnel.

7. A method according to claim 6 further comprising the step of inserting said first device until it contacts said second device.

8. A method according to claim 6 wherein said first device is an interference screw.

9. A method of securing a ligament graft having a first end and a second end within a bone tunnel, said bone tunnel having a peripheral wall and having a first distal end and a second proximal end, said method comprising the steps of:
   attaching a secondary surgical implant to said first end of said ligament graft, said secondary surgical implant comprising a body having a predetermined size small enough to enable said body to fit within said bone tunnel distal end but too large to pass said below-mentioned primary surgical implant;
   placing said first end of said ligament graft, with said secondary surgical implant distally attached thereto, adjacent said first end of said tunnel; and securing said first end of said ligament graft within said first end of said bone tunnel by constricting it with a primary surgical implant interposed between said first end of said ligament graft and said peripheral wall.

10. A method according to claim 9 wherein said bone tunnel has a predetermined uniform diameter along its length and wherein said secondary surgical implant comprises, in a plane transverse to said tunnel, at least one dimension less than or equal to said predetermined diameter to enable said secondary surgical implant to be placed at said first distal end of said bone tunnel by passing through said second proximal end of said bone tunnel.

11. A method according to claim 9 wherein said primary surgical implant is an interference screw and wherein the said body of said secondary surgical implant is spherical and has a diameter greater than the distance between said interference screw and the wall of said bone tunnel opposite therefrom.

* * * * *